(12) United States Patent
Audousset

(10) Patent No.: US 7,875,084 B2
(45) Date of Patent: Jan. 25, 2011

(54) COMPOSITION FOR THE OXIDATION DYEING OF KERATIN FIBERS COMPRISING AT LEAST ONE NONIONIC DERIVATIVE OF CELLULOSE WITH AT LEAST ONE HYDROPHOBIC SUBSTITUENT, AT LEAST ONE NONIONIC, NONHYDROPHOBIC POLYMER OF THE HYDROXYALKYLCELLULOSE TYPE, AND AT LEAST ONE OXIDATION DYE, AND OXIDATION DYEING PROCESS

(75) Inventor: Marie-Pascale Audousset, Asnieres (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/267,764

(22) Filed: Nov. 10, 2008

(65) Prior Publication Data

US 2009/0151088 A1 Jun. 18, 2009

Related U.S. Application Data

(60) Provisional application No. 60/996,650, filed on Nov. 28, 2007.

(30) Foreign Application Priority Data

Nov. 9, 2007 (FR) .................................. 0758912

(51) Int. Cl.
*A61Q 5/10* (2006.01)
(52) U.S. Cl. ..................... 8/405; 8/406; 8/410; 8/411; 8/412; 8/421; 8/435; 8/552; 8/559
(58) Field of Classification Search ................ 8/405, 8/406, 410, 411, 412, 421, 435, 552, 559
See application file for complete search history.

(56) References Cited

U.S. PATENT DOCUMENTS

| | | | |
|---|---|---|---|
| 4,370,142 A * | 1/1983 | Bugaut et al. ............... | 8/407 |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 6,010,541 A | 1/2000 | De la Mettrie et al. | |
| 7,285,137 B2 | 10/2007 | Vidal et al. | |
| 7,306,630 B2 | 12/2007 | Audousset | |
| 7,329,287 B2 | 2/2008 | Simonet et al. | |
| 7,410,505 B2 | 8/2008 | Cottard et al. | |
| 7,485,156 B2 | 2/2009 | Saunier | |
| 7,569,078 B2 | 8/2009 | Legrand | |
| 2001/0023515 A1 * | 9/2001 | Cottard et al. ............... | 8/406 |
| 2005/0166335 A1 | 8/2005 | Vidal et al. | |
| 2005/0169871 A1 | 8/2005 | De La Mettrie | |
| 2006/0260071 A1 | 11/2006 | Legrand | |
| 2007/0050924 A1 | 3/2007 | Cotteret | |

FOREIGN PATENT DOCUMENTS

| | | |
|---|---|---|
| DE | 41 33 957 | 4/1993 |
| DE | 42 34 887 | 4/1994 |
| EP | 0 375 977 | 7/1990 |
| EP | 1 426 038 | 6/2004 |
| EP | 1 426 040 | 6/2004 |
| EP | 1 473 025 | 11/2004 |
| EP | 1 550 656 | 7/2005 |
| EP | 1 566 164 | 8/2005 |
| EP | 1 707 190 | 10/2006 |
| EP | 1 733 716 | 12/2006 |
| WO | WO 98/03150 | 1/1998 |
| WO | WO 02/051372 | 7/2002 |

OTHER PUBLICATIONS

Copending U.S. Appl. No. 12/267,786, filed Nov. 10, 2008.
French Search Report for FR 07/58912, dated Jun. 25, 2008.
French Search Report for FR 07/58914, dated Jun. 17, 2008.
Office Action mailed Jun. 3, 2009, in co-pending U.S. Appl. No. 12/267,786.
Office Action mailed Nov. 20, 2009, in co-pending U.S. Appl. No. 12/267,786.
Office Action mailed May 13, 2010, in co-pending U.S. Appl. No. 12/267,786.

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

The present disclosure relates to a dye composition for keratin fibers, including human keratin fibers such as the hair, comprising, in a medium suitable for dyeing: (A) at least one nonionic derivative of cellulose comprising at least one hydrophobic substituent containing from 8 to 30 carbon atoms; (B) at least one nonionic, nonhydrophobic polymer of the hydroxyalkylcellulose type; and (C) at least one oxidation dye. The present disclosure also relates to a process for dyeing keratin fibers using such a composition; and also to a device that uses this composition for dyeing keratinous fibers.

22 Claims, No Drawings

COMPOSITION FOR THE OXIDATION DYEING OF KERATIN FIBERS COMPRISING AT LEAST ONE NONIONIC DERIVATIVE OF CELLULOSE WITH AT LEAST ONE HYDROPHOBIC SUBSTITUENT, AT LEAST ONE NONIONIC, NONHYDROPHOBIC POLYMER OF THE HYDROXYALKYLCELLULOSE TYPE, AND AT LEAST ONE OXIDATION DYE, AND OXIDATION DYEING PROCESS

This application claims benefit of U.S. Provisional Application No. 60/996,650, filed Nov. 28, 2007, the contents of which are incorporated herein by reference. This application also claims benefit of priority under 35 U.S.C. §119 to French Patent Application No. FR 0758912, filed Nov. 9, 2007, the contents of which are also incorporated herein by reference.

Disclosed herein is a composition for the oxidation dyeing of keratin fibers, including human keratin fibers such as hair, comprising at least one nonionic derivative of cellulose modified with at least one specific hydrophobic group, at least one nonionic, nonhydrophobic polymer of the hydroxyalkylcellulose type, and at least one oxidation dye.

Also disclosed herein is the use of this composition for dyeing keratin fibers and also to the dyeing process using this composition.

It is known practice to dye keratin fibers, including human hair, with dye compositions containing oxidation dye precursors, generally known as oxidation bases, such as ortho- or para-phenylenediamines, ortho- or para-aminophenols and heterocyclic compounds. These oxidation bases are colorless or weakly colored compounds which, in combination with oxidizing products, can give rise, by means of an oxidative condensation process, to colored compounds.

It is also known that it is possible to vary the shades obtained with these oxidation bases by combining them with couplers or coloring modifiers, the latter being chosen for example, from aromatic meta-diamines, meta-aminophenols, meta-diphenols and certain heterocyclic compounds such as indole compounds.

The variety of the molecules available as oxidation bases and couplers makes it possible to obtain a rich palette of colors.

The "permanent" coloring obtained by virtue of these oxidation dyes may, moreover, meet a certain number of requirements.

Thus, for example, it may have no toxicological drawbacks, it may allow shades to be obtained in the desired strength, and it may show good fastness with respect to external agents such as light, bad weather, washing, permanent-waving, perspiration and rubbing.

The dyes may also allow white hair to be covered and, finally, may be as nonselective as possible, i.e. they should make it possible to obtain the smallest possible differences in coloring along the same keratin fiber, which is generally differently sensitized (i.e. damaged) between its tip and its root.

Moreover, the compositions obtained may have good rheological properties, while at the same time conserving good coloring properties. For example, these compositions may not run on the face or out of the areas intended to be dyed, for example when they are applied after mixing with an oxidizing agent.

Improving the power of dyeing by combining a para-phenylenediamine oxidation base and at least one nonionic amphiphilic polymer such as hydroxycellulose modified with a hydrophobic group is discussed in International Patent Application Publication No. WO 98/03150.

However, these compositions do not entirely meet the above-mentioned requirements and can be improved, especially in terms of dyeing properties, for example in terms of dyeing selectivity and fastnesses. Thus, there is a need in the art for stable hair dyeing compositions, for example in the form of creams, which are easy to prepare and to apply, which have good rheological qualities and which produce strong, relatively nonselective colorations that withstand the various attacks that keratin fibers may be subjected to.

Accordingly, one aspect of the present disclosure is a dye composition for keratin fibers, including human keratin fibers such as the hair, that meets at least one of the conditions discussed above, comprising, in a medium suitable for dyeing:

(A) at least one nonionic derivative of cellulose comprising at least one hydrophobic substituent containing from 8 to 30 carbon atoms;

(B) at least one nonionic, nonhydrophobic polymer of the hydroxyalkylcellulose type; and (C) at least one oxidation dye.

The dye compositions according to the present disclosure may have for example at least one of the following properties:

they make it possible to obtain compositions with a viscosity corresponding to a cream, which are stable over time, they stand out by virtue of the fact that they could be easily mixed with the oxidizing composition, they stand out by virtue of the rheological qualities of the creams obtained (good viscosity of cream as a mixture), they are easy to apply after mixing with the oxidizing composition at the time the dyeing is carried out (qualities of use on the head).

In addition, the compositions according to the present disclosure may make it possible to obtain compositions capable of producing colorings with varied, chromatic, powerful, aesthetic and relatively nonselective shades which are uniform over all the keratin fibers, including human keratin fibers such as the hair, and which are highly resistant to the various attacks to which the fibers may be subjected.

Another aspect of the present disclosure comprises a process for dyeing keratin fibers, in which a cosmetic composition according to the present disclosure is used.

Still another aspect of the present disclosure relates to the use of this cosmetic composition for dyeing keratin fibers, for example human keratin fibers, such as the hair.

Other features, aspects, subjects and benefits of the present disclosure will emerge more clearly on reading the description and the non-limiting examples which follow.

Unless otherwise indicated, the limits of the ranges of values which are given in the context of the present disclosure are included in these ranges.

The term "at least one derivative of cellulose" is intended to mean at least one compound comprising at least one cellobiose unit having the following structure:

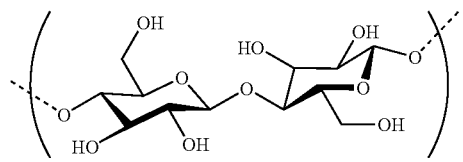

in which at least one hydroxyl groups may be substituted.

The at least one nonionic derivative of cellulose with at least one hydrophobic substituent (A) in accordance with the present disclosure is chosen from amphiphilic polymers that are associative in nature. They may comprise hydrophilic units and hydrophobic units and are capable of interacting and of associating with one another or with other molecules, reversibly, for example, by virtue of the presence of their hydrophobic chains.

In one aspect of the present disclosure, the at least one cellulose derivative of the present disclosure is a cellulose ether comprising at least one hydrophobic substituent containing from 8 to 30 carbon atoms.

The at least one nonionic derivative of cellulose with at least one hydrophobic substituent in accordance with the present disclosure is generally prepared from water-soluble nonionic ethers of cellulose, in which all or some of the reactive hydroxyl functional groups are substituted with at least one hydrophobic chain containing from 8 to 30 carbon atoms, for example from 10 to 22 carbon atoms, such as 16 carbon atoms. The reaction steps involved in the preparation of the cellulose derivatives of the present disclosure are known to those skilled in the art.

The nonionic ethers of cellulose chosen for preparing the at least one nonionic derivative of cellulose with at least one hydrophobic substituent according to the present disclosure has, for example, a degree of nonionic substitution, for example of methyl, hydroxyethyl or hydroxypropyl groups, that is sufficient to be water-soluble, i.e. to form a substantially clear solution when they are dissolved in water at 25° C. at the concentration of 1% by weight.

The nonionic ethers of cellulose chosen for preparing the at least one nonionic derivative of cellulose with at least one hydrophobic substituent according to the present disclosure can have a relatively low number-average molar mass, for example, of less than 800,000 g/mol, for instance ranging from 50,000 to 700,000 g/mol, such as ranging from 200,000 to 600,000 g/mol.

In at least one embodiment of the present disclosure, the cellulose derivative of the present disclosure is a hydroxyethylcellulose comprising at least one hydrophobic substituent containing from 8 to 30 carbon atoms.

The at least one nonionic derivative of cellulose used according to the present disclosure is substituted with at least one aliphatic or aromatic, saturated or unsaturated, linear, branched or cyclic $C_8$-$C_{30}$ hydrocarbon chain, that may be attached to the cellulose ether substrate via an ether, ester or urethane bond, for example, in at least one embodiment, an ether bond.

According to at least one embodiment, the at least one hydrophobic substituent used as a substituent of the at least one nonionic derivative of cellulose according to the present disclosure is chosen from $C_8$-$C_{30}$, for example $C_{10}$-$C_{22}$, alkyl, arylalkyl and alkylaryl group.

According to at least one embodiment of the present disclosure, the at least one hydrophobic substituent according to the present disclosure is chosen from saturated alkyl chain.

According to at least one embodiment, the at least one hydrophobic substituent according to the present disclosure is chosen from cetyl group.

The at least one nonionic derivative of cellulose with at least one hydrophobic substituent according to the present disclosure has a viscosity of, for example, ranging from 100 to 100,000 mPa·s, such as from 200 to 20,000 mPa·s, measured at 25° C. in a solution at 1% by weight of polymer in water, this viscosity being determined conventionally using a Brookfield LVT viscometer at 6 rpm with the No. 3 spindle.

The degree of hydrophobic substitution of the at least one hydrophilic nonionic derivative of cellulose used according to the present disclosure can range from 0.1% to 10% by weight, for example from 0.1% to 1% by weight, such as from 0.4% to 0.8% by weight, of the total weight of the polymer.

Among the at least one nonionic derivative of cellulose with at least one hydrophobic substituent that can be used in the compositions of the present disclosure, non-limiting mention may be made of the cetyl hydroxyethylcelluloses sold under the names NATROSOL PLUS GRADE 330 CS and POLYSURF 67 CS (INCI: Cetyl Hydroxyethylcellulose) by the company Aqualon/Hercules.

The concentration of the at least one nonionic derivative of cellulose with at least one hydrophobic substituent (A) of the compositions according to the present disclosure can range from 0.01% to 10% by weight, for example from 0.05% to 3% by weight, such as from 0.1% to 1% by weight, relative to the total weight of the composition.

For the purpose of the present disclosure, the term "at least one nonhydrophobic polymer" is intended to mean at least one polymer which does not comprise, in its structure, a fatty chain containing at least 8 carbon atoms.

The at least one nonionic, nonhydrophobic polymer of the hydroxyalkylcellulose type (B) that can be used according to the present disclosure is prepared from cellulose of which all or some of the hydroxyl functional groups are etherified, in a manner known to those skilled in the art, with at least one alkyl or hydroxyalkyl group, which may be identical or different, for example containing from 1 to 4 carbon atoms.

The at least one nonionic, nonhydrophobic polymer of the hydroxyalkylcellulose type (B) that can be used according to the present disclosure thus comprise at least one group chosen from linear and branched, saturated and unsaturated, alkyl and hydroxyalkyl groups, which may be identical or different, for example containing from 1 to 4 carbon atoms.

Of the at least one alkyl or hydroxyalkyl group containing from 1 to 4 carbon atoms, that can be used, non-limiting mention may be made of methyl, ethyl, propyl, isopropyl, hydroxymethyl, hydroxyethyl, hydroxypropyl and hydroxyisopropyl groups.

The at least one nonionic, nonhydrophobic polymer of the hydroxyalkylcellulose type (B) according to the present disclosure can be, by way of non-limiting example, chosen from:

hydroxypropylmethylcelluloses, such as those sold under the name METHOCEL F4M by the company Dow Chemical, and hydroxyethylcelluloses, such as those sold under the name NATROSOL 250 HHR by the company Aqualon.

In at least one embodiment, the at least one nonionic, nonhydrophobic polymer of the hydroxyalkylcellulose type (B) is hydroxypropylmethylcellulose.

The at least one nonionic, nonhydrophobic polymer of the hydroxyalkylcellulose type (B) of the compositions according to the present disclosure can be present in an amount ranging from 0.01% to 5%, for example from 0.05% to 2% by weight, such as from 0.1% to 1% by weight, relative to the total weight of the composition.

The at least one oxidation dye (C) that can be used according to the present disclosure can be chosen from oxidation bases, oxidation couplers, and addition salts thereof.

By way of non-limiting example, the at least one oxidation base can be chosen from para-phenylenediamines, bisphenylalkylenediamines, para-aminophenols, bis-para-aminophenols, ortho-aminophenols, heterocyclic bases, and addition salts thereof.

Among the para-phenylenediamines, mention may be made, by way of non-limiting example, of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis (β-hydroxyethyl)-para-phenylenediamine, 4-N,N-bis(β-hydroxyethyl)amino-2-methylaniline, 4-N,N-bis(μ-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-p-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and acid addition salts thereof.

Among the para-phenylenediamines mentioned above, further non-limiting mention may be made of para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and acid addition salts thereof.

Among the bisphenylalkylenediamines, mention may, by way of non-limiting example, be made of N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis (4-amino-phenyl)tetramethylenediamine, N,N'-bis-(4-methylaminophenyl)tetramethylenediamine, N,N'-bis (ethyl)-N,N'-bis(4'-amino-3'-methylphenyl)ethylenediamine, 1,8-bis(2,5-diaminophenoxy)-3,6-dioxaoctane and acid addition salts thereof.

Among the para-aminophenols, mention may be made, by way of non-limiting example of para-aminophenol, 4-amino-3-methylphenol, 4-amino-3-fluorophenol, 4-amino-3-hydroxymethyl phenol, 4-amino-2-methylphenol, 4-amino-2-hydroxymethyl phenol, 4-amino-2-methoxymethylphenol, 4-amino-2-aminomethylphenol, 4-amino-2-(β-hydroxyethylaminomethyl)phenol, 4-amino-2-fluorophenol, and acid addition salts thereof.

Among the ortho-aminophenols, mention may, by way of non-limiting example, be made of 2-aminophenol, 2-amino-5-methylphenol, 2-amino-6-methylphenol, 5-acetamido-2-aminophenol, and acid addition salts thereof.

Among the heterocyclic bases, mention may, by way of non-limiting example, be made of pyridine derivatives, pyrimidine derivatives, pyrazole derivatives, pyrazolone derivatives, and addition salts thereof.

Among the pyridine derivatives, non-limiting mention may be made of the compounds described, for example, in British Patent Nos. GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl) amino-3-amino-6-methoxypyridine, 3,4-diaminopyridine, and acid addition salts thereof.

Other non-limiting examples of pyridine oxidation bases that can be used in the present disclosure are the 3-aminopyrazolo[1,5-a]pyridine oxidation bases or addition salts thereof described, for example, in French Patent Application Publication FR 2801308. By way of non-limiting example, mention may be made of pyrazolo[1,5-a]pyridin-3-ylamine; 2-acetylaminopyrazolo-[1,5-a]pyridin-3-ylamine; 2-morpholin-4-ylpyrazolo[1,5-a]pyridin-3-ylamine; 3-aminopyrazolo[1,5-a]pyridine-2-carboxylic acid; 2-methoxypyrazolo [1,5-a]pyridin-3-ylamino; (3-aminopyrazolo[1,5-a]pyridin-7-yl)methanol; 2-(3-aminopyrazolo[1,5-a]pyridin-5-yl) ethanol; 2-(3-aminopyrazolo[1,5-a]pyridin-7-yl)ethanol; (3-aminopyrazoto[1,5-a]pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo[1,5-a] pyridine-3,5-diamine; 5-morpholin-4-ylpyrazolo[1,5-a] pyridin-3-yl-amine; 2-[(3-aminopyrazolo[1,5-a]pyridin-5-yl)(2-hydroxyethyl)amino]ethanol; 2-[(3-aminopyrazolo[1, 5-a]pyridin-7-yl)(2-hydroxyethyl)amino]ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-aminopyrazolo[1,5-a]pyridin-7-ol; and also acid or base addition salts thereof.

Among the pyrimidine derivatives, non-limiting mention may be made of the compounds described, for example, in Patents DE 2359399; JP 88-169571; JP 05-63124; EP 0770375 or Patent Application Publication WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives such as those mentioned in Patent Application Publication FR-A-2 750 048 and among which non-limiting mention may be made of pyrazolo[1,5-a]-pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo [1,5-a]pyrimidin-7-ylamino)ethanol, 2-(7-aminopyrazolo[1, 5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl) amino]ethanol, 5,6-dimethyl-pyrazolo[1,5-a]pyrimidine-3,7-diamine, 2,6-dimethylpyrazolo[1,5-a]pyrimidine-3,7-diamine, 2, 5, N7, N7-tetramethylpyrazolo[1,5-a] pyrimidine-3,7-diamine, 3-amino-5-methyl-7-imidazolylpropylaminopyrazolo[1,5-a]pyrimidine, and acid addition salts thereof and tautomeric forms thereof when a tautomeric equilibrium exists.

Among the pyrazole derivatives that can be used, non-limiting mention may be made, for example, of the compounds described in patent application publications DE-A-38 43 892, DE-A-41 33 957, WO 94/08969, WO 94/08970, FR-A-2 733 749, and DE-A-195 43 988, such as 4,5-diamino-1-methylpyrazole, 4,5-diamino-1-(β-hydroxyethyl)-pyrazole, 3,4-diaminopyrazole, 4,5-diamino-1-(4'-chlorobenzyl) pyrazole, 4,5-diamino-1,3-dimethylpyrazole, 4,5-diamino-3-methyl-1-phenylpyrazole, 4,5-diamino-1-methyl-3-phenyl-pyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methyl-pyrazole, 4,5-diamino-1-(β-hydroxyethyl)-3-methylpyrazole, 4,5-diamino-1-ethyl-3-methyl-pyrazole, 4,5-diamino-1-ethyl-3-(4'- methoxyphenyl)pyrazole, le 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and addition salts thereof.

Among the pyrazolone derivatives that can be used, non-limiting mention may, for example, be made of the following compounds and addition salts thereof:

2,3-diaminodihydropyrazolone;
4,5-diamino-1,2-dimethyl-1,2-dihydropyrazole-3-one;
4-amino-5-methylamino-1,2-dimethyl-1,2-dihydropyrazole-3-one;
4-amino-5-dimethylamino-1,2-dimethyl-1,2-dihydropyrazole-3-one;
4-amino-5-(2-hydroxyethyl)amino-1,2-dimethyl-1,2-dihydropyrazole-3-one;
4-amino-5-(pyrrolidin-1-yl)-1,2-dimethyl-1,2-dihydropyrazole-3-one;
4-amino-5-(piperidin-1-yl)-1,2-dimethyl-1,2-dihydropyrazole-3-one;
4,5-diamino-1,2-di(2-hydroxyethyl)-1,2-dihydropyrazole-3-one;
4-amino-5-methylamino-1,2-di(2-hydroxyethyl)-1,2-dihydropyrazole-3-one;
4-amino-5-dimethylamino-1,2-di(2-hydroxyethyl)-1,2-dihydropyrazole-3-one;
4-amino-5-(2-hydroxyethyl)amino-1,2-di(2-hydroxyethyl)-1,2-dihydropyrazole-3-one;
4-amino-5-(pyrrolidin-1-yl)-1,2-di(2-hydroxyethyl)-1,2-dihydropyrazole-3-one;
4-amino-5-(piperidin-1-yl)-1,2-di(2-hydroxyethyl)-1,2-dihydropyrazole-3-one;
4,5-diamino-1,2-diethyl-1,2-dihydropyrazole-3-one;
4,5-diamino-1,2-diphenyl-1,2-dihydropyrazole-3-one;
4,5-diamino-1-ethyl-2-methyl-1,2-dihydropyrazole-3-one;
4,5-diamino-2-ethyl-1-methyl-1,2-dihydropyrazole-3-one;
4,5-diamino-1-phenyl-2-methyl-1,2-dihydropyrazole-3-one;
4,5-diamino-2-phenyl-1-methyl-1,2-dihydropyrazole-3-one;
4,5-diamino-1-(2-hydroxyethyl)-2-methyl-1,2-dihydropyrazole-3-one;
4,5-diamino-2-(2-hydroxyethyl)-1-methyl-1,2-dihydropyrazole-3-one;
2,3-diamino-6,7-dihydro-1H,5H-pyrazolo[1,2-a]pyrazol-1-one;
2-amino-3-methylamino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(2-hydroxyethyl)amino-6,7-dihydro-1H,5H-pyrazolo[1,2-a]pyrazol-1-one;
2-amino-3-(2-hydroxypropyl)amino-6,7-dihydro-1H,5H-pyrazolo[1,2-a]pyrazol-1-one;
2-amino-3-bis(2-hydroxyethyl)amino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
2-amino-3-(3-hydroxypyrrolidin-1-yl)-6,7-dihydro-1H,5H-pyrazolo[1,2-a]pyrazol-1-one,
2-amino-3-(piperidin-1-yl)-6,7-dihydro-1H,5H-pyrazolo[1,2-a]pyrazol-1-one;
2,3-diamino-6-hydroxy-6,7-dihydro-1H,5H-pyrazolo[1,2-a]pyrazol-1-one;
2,3-diamino-6-methyl-6,7-dihydro-1H,5H-pyrazolo[1,2-a]pyrazol-1-one;
2,3-diamino-6,6-dimethyl-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
2,3-diamino-5,8-dihydro-1H,6H-pyridazino[1,2-a]pyrazol-1-one;
4-amino-5-dimethylamino-1,2-diethyl-1,2-dihydropyrazole-3-one;
4-amino-1,2-diethyl-5-ethylamino-1,2-dihydropyrazole-3-one;
4-amino-1,2-diethyl-5-isopropylamino-1,2-dihydropyrazole-3-one;
4-amino-1,2-diethyl-5-(2-hydroxyethylamino)-1,2-dihydropyrazole-3-one;
4-amino-5-(2-dimethylaminoethylamino)-1,2-diethyl-1,2-dihydropyrazole-3-one;
4-amino-5-[bis(2-hydroxyethyl)amino]-1,2-diethyl-1,2-dihydropyrazole-3-one;
4-amino-1,2-diethyl-5-(3-imidazol-1-ylpropylamino)-1,2-dihydropyrazole-3-one;
4-amino-1,2-diethyl-5-(3-hydroxypyrrolidin-1-yl)-1,2-dihydropyrazole-3-one;
4-amino-5-pyrrolidin-1-yl-1,2-diethyl-1,2-dihydropyrazole-3-one;
4-amino-5-(3-dimethylaminopyrrolidin-1-yl)-1,2-diethyl-1,2-dihydropyrazole-3-one; and
4-amino-1,2-diethyl-5-(4-methylpiperazin-1-yl)pyrazolidin-3-one.

The at least one oxidation base can be present in an amount ranging from 0.001% to 20% by weight, for example from 0.005% to 10% by weight, such as from 0.1% to 5% by weight, relative to the total weight of the composition.

The at least one oxidation coupler present in the compositions of the present disclosure may be chosen from benzene couplers, heterocyclic couplers, naphthalene couplers, and addition salts thereof.

By way of benzene couplers that can be used in the compositions according to the present disclosure, non-limiting mention may be made of meta-aminophenols, meta-phenylenediamines, meta-diphenols, and also addition salts thereof.

Among the couplers, further non-limiting mention may be made of 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methyl indole, 2-amino-3-hydroxypyridine, 6-hydroxybenzomorpholine 3,5-diamino-2,6-dimethoxypyridine, 1-N-(β-hydroxyethyl)amino-3,4-methylenedioxybenzene, 2,6-bis-(β-hydroxyethylamino)toluene, and acid addition salts thereof.

The at least one oxidation coupler can be present in an amount ranging from 0.001% to 20% by weight, for example from 0.005% to 10% by weight, such as from 0.01% to 5% by weight, relative to the total weight of the composition.

According to one aspect of the present disclosure, the dye compositions of the present disclosure comprise, in a medium suitable for dyeing:

(A) at least one nonionic derivative of cellulose comprising at least one hydrophobic substituent containing from 8 to 30 carbon atoms as defined above;

(B) at least one nonionic, nonhydrophobic polymer of the hydroxyalkylcellulose type; and (C) at least one oxidation base and at least one oxidation coupler.

The addition salts of the oxidation bases and of the couplers that can be used in the context of the present disclosure are, for example, chosen from the acid addition salts, such as the hydrochlorides, hydrobromides, sulphates, citrates, succinates, tartrates, lactates, tosylates, benzenesulphonates, phosphates and acetates, and the basic addition salts, such as sodium hydroxide, potassium hydroxide, aqueous ammonia, amines or alkanolamines.

The dye composition in accordance with the present disclosure may also comprise at least one direct dye that may, for example, be chosen from nitrobenzene dyes, azo direct dyes, methine direct dyes, anthraquinone dyes, xanthene dyes, triarylmethane dyes, and addition salts thereof. These direct dyes may be nonionic, anionic or cationic in nature.

The medium used in the compositions according to the present disclosure can be an aqueous medium, or a medium comprising water and at least one organic solvent.

The at least one organic solvent used in the compositions according to the present disclosure may be chosen from monohydroxylated alcohols and polyols.

By way of monohydroxylated alcohols that can be used, non-limiting mention may be made, for example, of $C_1$-$C_4$ lower alcohols such as ethanol, isopropanol, tert-butanol or n-butanol, and mixtures thereof.

By way of polyols that can be used, non-limiting mention may be made, for example, of propylene glycol, polyethylene glycols and glycerol. By way of organic solvents, non-limiting mention may also be made, for example, of polyol ethers such as 2-butoxyethanol, propylene glycol monomethyl ether, diethylene glycol monoethyl ether and diethylene glycol monomethyl ether, and also aromatic alcohols such as benzyl alcohol or phenoxyethanol, and mixtures thereof.

The at least one organic solvent in the compositions according to the present disclosure can be present in an amount ranging from 0 to 30%, for example from 0 to 20% by weight, relative to the total weight of the composition.

The compositions according to the present disclosure may also comprise at least one thickener, also referred to as "at least one rheology-adjusting agent," different from the at least one nonionic derivative of cellulose having at least one hydrophobic substituent of the present disclosure.

The at least one rheology-adjusting agent may be chosen from mineral or organic thickeners, for example polymeric associative thickeners, fatty alcohols (oleyl alcohol), cellulosic derivatives other than the at least one nonionic derivative of cellulose with at least one hydrophobic substituent (A) and the at least one nonionic, nonhydrophobic polymer of the hydroxyalkylcellulose type (B) according to the present disclosure (carboxymethylcellulose) and gums of microbial origin (xanthan gum, scleroglucan gum).

For example the at least one rheology-adjusting agent can be chosen from fatty alcohols, for example $C_{20}$-$C_{22}$ fatty alcohols, and cellulose derivatives, other than the at least one nonionic derivative of cellulose with at least one hydrophobic substituent (A) and the at least one nonionic, nonhydrophobic polymer of the hydroxyalkylcellulose type (B) according to the present disclosure.

The at least one thickener can be present in an amount ranging from 0.01% to 20% by weight, for example from 1% to 10% by weight, relative to the total weight of the composition.

The dye composition in accordance with the present disclosure may also comprise at least one adjuvant conventionally used in compositions for dyeing the hair.

The term "adjuvant" is intended to mean at least one additive different from the abovementioned compounds, such as anionic, cationic, nonionic, amphoteric or zwitterionic surfactants or mixtures thereof; nonionic, amphoteric, zwitterionic, anionic or cationic polymers, other than the at least one nonionic derivative of cellulose with at least one hydrophobic substituent (A) and the at least one nonionic, nonhydrophobic polymer of the hydroxyalkylcellulose type (B) according to the present disclosure, or mixtures of said polymers; penetrating agents; sequestering agents; fragrances; buffers; dispersants; conditioning agents such as, for example, modified or unmodified, volatile or non-volatile silicones; film-forming agents; ceramides, preservatives; opacifiers; vitamins; amino acids; oligopeptides; peptides; modified or unmodified, hydrolysed or nonhydrolysed proteins; enzymes; branched or unbranched fatty acids and alcohols; animal, plant or mineral waxes; hydroxylated organic acids; UV screens; antioxidants and free-radical scavengers; antidandruff agents; seborrhea-regulating agents; calmatives; animal, plant or mineral oils; polyisobutenes and poly($\alpha$-olefins); pigments; acids, bases, plasticizers, mineral fillers, pearlescent agents, flakes; antistatic agents and reducing agents.

The at least one adjuvant can be present in an amount, for each of them, for example ranging from 0.01% to 40% by weight, such as from 0.1% to 25% by weight, relative to the total weight of the composition.

Of course, those skilled in the art will take care to select this (or these) possible additional compound(s) in such a way that the beneficial properties intrinsically associated with the oxidation dyeing composition in accordance with the present disclosure are not, or not substantially, impaired by the addition(s) envisaged.

The pH of the dye composition in accordance with the present disclosure generally ranges from 3 to 12, for example from 5 to 11. It may be adjusted to the desired value via at least one acidifying agent or at least one basifying agent commonly used in the dyeing of keratin fibers or alternatively using at least one conventional buffer system.

Among the acidifying agents, mention may be made, by way of non-limiting example, of mineral or organic acids such as hydrochloric acid, orthophosphoric acid, sulphuric acid, sulphonic acids and carboxylic acids, for instance acetic acid, tartaric acid, citric acid and lactic acid.

Among the basifying agents, mention may, by way of non-limiting example, be made of aqueous ammonia, alkali metal carbonates, alkanolamines such as mono-, di- and tri-ethanolamines and derivatives thereof, sodium hydroxide or potassium hydroxide and the compounds of formula (I):

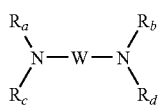

wherein:
W is a propylene residue optionally substituted with a hydroxyl group or a $C_1$-$C_4$ alkyl group;
$R_a$, $R_b$, $R_c$ and $R_d$, which may be identical or different, are chosen from hydrogen atoms, $C_1$-$C_4$ alkyl groups, and $C_1$-$C_4$ hydroxyalkyl groups.

The dye composition according to the present disclosure may be in various forms, such as in the form of creams or gels, or in any other form suitable for dyeing keratin fibers, including human hair.

The process for dyeing keratin fibers, of the present disclosure, is a process in which the composition according to the present disclosure is applied to the fibers, for example in the presence of at least one oxidizing agent, for a period of time sufficient to develop the desired color. The color may be revealed at acidic, neutral or alkaline pH and the at least one oxidizing agent may be added to the composition of the present disclosure just at the time of use, or it may be used starting from an oxidizing composition comprising it, applied simultaneously with or sequentially to the composition of the present disclosure.

According to another aspect of the present disclosure, the composition according to the present disclosure is a ready-to-use composition, wherein the dye composition is mixed, for example at the time of use, with a composition comprising, in a medium suitable for dyeing, at least one oxidizing agent, wherein the at least one oxidizing agent is present in a sufficient amount to develop a coloration. The mixture obtained is subsequently applied to the keratin fibers. After a leave-on time of, for example, 3 to 50 minutes, such as 5 to 30 minutes, the keratin fibers are rinsed, washed with shampoo, rinsed again, and then dried.

The oxidizing agents conventionally used for the oxidation dyeing of keratin fibers are, for example, hydrogen peroxide, urea peroxide, alkali metal bromates, persalts such as perborates and persulphates, peracids and oxidase enzymes, among which mention may be made of peroxidases, 2-electron oxidoreductases, such as uricases, and 4-electron oxygenases, such as laccases, these oxidoreductases being optionally combined with their customary cofactors, such as uric acid for uricases. For example, in at least one embodiment, the oxidizing agent can be hydrogen peroxide.

The oxidizing composition may also contain at least one adjuvant used in compositions for dyeing the hair, as defined above.

The pH of the oxidizing composition comprising the at least one oxidizing agent is such that, after mixing with the dye composition, the pH of the resulting composition applied to the keratin fibers ranges, for example, from 3 to 12, such as from 5 to 10. It may be adjusted to the desired value via at least one acidifying agent or at least one basifying agent normally used in the dyeing of keratin fibers, as defined above.

The ready-to-use composition which is finally applied to the keratin fibers may be in various forms, such as in the form of creams or gels, or in any other form suitable for dyeing keratin fibers, for example human keratin fibers such as the hair.

Another aspect of the present disclosure is also a multi-compartment dyeing device or dyeing "kit," comprising at least one first compartment containing at least one dye composition as defined above, and at least one second compartment containing at least one oxidizing composition. This device may be equipped with a mechanism for delivering the desired mixture to the hair, such as the devices described in French Patent Application No. FR-A-2 586 913.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples which follow serve to illustrate the invention without, however, being limiting in nature.

EXAMPLES

Example 1

Dye Compositions According to the Present Disclosure

The following compositions 1 and 2 according to the present disclosure were prepared

|  | Dye composition | |
|---|---|---|
|  | Composition 1 | Composition 2 |
| Cetyl hydroxyethylcellulose (POLYSURF 67 sold by the company Aqualon) | 0.4 g | — |
| Cetyl hydroxyethylcellulose (NATROSOL PLUS GRADE 330 CS sold by the company Aqualon) | — | 0.4 g |
| Hydroxypropylmethylcellulose | 0.19 g | 0.19 g |
| p-aminophenol | 0.1 g | — |
| p-phenylenediamine | — | 0.3 g |
| 2,3-diaminodihydropyrazolopyrazolone dimethosulfate | 1.9 g | — |
| 4,5-diamino-1-(β-hydroxyethyl)pyrazole sulfate | — | 1.9 g |
| 4-amino-2-hydroxytoluene | 0.2 g | 1.4 g |
| 5-amino-6-chloro-o-cresol | 0.8 g | 0.2 g |
| Stearic acid monoethanolamide | 4.8 g | 4.8 g |
| Oleic acid | 3 g | 3 g |
| Aqueous solution containing 20% by weight of $NH_3$ | 7 g | 2.06 g |
| $TiO_2$ | 0.3 g | 0.3 g |
| Monoethanolamine | 6.47 g | 6.28 g |
| Oleth-10 | 1.8 g | 1.8 g |
| Aqueous solution containing 40% by weight of Polyquaternium-6 (MERQUAT 100 sold by the company Ondeo) | 1.6 g | 1.6 g |
| Ethylenediaminetetraacetic acid (EDTA) | 0.2 g | 0.2 g |

-continued

| | Dye composition | |
|---|---|---|
| | Composition 1 | Composition 2 |
| Aqueous solution of 60% by weight of hexadimethrine chloride (MEXOMERE PO sold by the company Chimex) | 1.2 g | 1.2 g |
| Oleth-30 | 1.5 g | 1.5 g |
| Steareth-2 | 5.5 g | 5.5 g |
| $C_{20}$-$C_{22}$ alcohols (NAFOL 2022 EN sold by the company Sasol) | 3 g | 3 g |
| Reducing agent | q.s. | — |
| Demineralized water q.s. | 100 g | 100 g |

Application Protocol

Each of composition 1 and 2 was diluted, extemporaneously, with one and a half times its weight of an oxidizing composition (pH in the region of 3) (aqueous hydrogen peroxide at 20 volumes) (6% by weight of $H_2O_2$). The mixture was prepared and had a good viscosity; it was easily applied to grey hair, containing 90% white hairs, at a rate of 10 g per 1 g of hair, for 30 minutes. The hair was then rinsed, washed with a standard shampoo and dried.

The hair coloration was evaluated visually. The results obtained on natural grey hair, containing 90% white hairs, after treatment, were the following:

| | Shade |
|---|---|
| Composition 1 | Strong coppery |
| Composition 2 | Strong coppery red |

These colorations had good properties, in particular in terms of selectivity and fastness. They also had a good strength. The compositions obtained were stable over time.

Example 2

Comparative Testing

Composition 3 according to the present disclosure and comparative Composition 4 were prepared.

| | Dye Composition | |
|---|---|---|
| | Composition 3 (present disclosure) | Composition 4 (comparative) |
| Ammonium hydroxide | 10 g | 10 g |
| Erythorbic acid | 0.50 g | 0.50 g |
| Ethanolamine | 0.70 g | 0.70 g |
| EDTA | 0.20 g | 0.20 g |
| Sodium sulphite | 0.50 g | 0.50 g |
| Titanium dioxide | 0.30 g | 0.30 g |
| 4-amino-2-hydroxytoluene | 0.25 g | 0.25 g |
| p-phenylenediamine | 0.22 g | 0.22 g |
| Cetearyl alcohol | 3 g | 3 g |
| Hydroxypropylmethylcellulose | 0.20 g | 0.20 g |
| Cetyl hydroxyethylcellulose | 0.40 g | — |
| Fatty-chain cationic polyurethane obtained from the condensation of 1,3-bis(isocyanatomethylcyclohexane), of N,N-dimethylethanolamine quaternized with bromododecane, of N,N-dimethylethanolamine and of polyoxyethylene with a molecular weight of 10,000 | — | 0.40 g |
| Oleic acid | 3 g | 3 g |
| Oxyethylenated stearyl alcohol comprising 2 mol of ethylene oxide | 5.50 g | 5.50 g |
| Stearamide monoethanolamine, monoethanolamine, stearic acid (96:2:2) | 5 g | 5 g |
| Oxyethylenated oleocetyl alcohol comprising 30 mol of ethylene oxide | 1.50 g | 1.50 g |
| Water | qs 100 g | qs 100 g |

Application Protocol

At the time of use, each of Compositions 3 and 4 was mixed with one and a half times its weight of an oxidizing composition (aqueous hydrogen peroxide at 20 volumes) (6% by weight of $H_2O_2$).

Rheological Property

The measurements were carried out on Compositions 3 and 4, before and after mixing with said oxidizing composition under the conditions described above.

The viscosity measurements were carried out using the RHEOMAT RM180 rheometer (Mettler): rotation speed 200 rpm and temperature at 25° C. with a different spindle according to viscosities (spindle No. 2, 3 or 4, noted respectively M1, M2 or M3). The viscosities were measured 30 seconds after the spindle had begun to rotate.

Results

| | Composition 3 | Composition 4 |
|---|---|---|
| Appearance of the composition before mixing | Thick cream | Fluid cream |
| Ease of mixing with the oxidizing composition | Acceptable | More rapid |
| Distribution on locks | Good | Good but composition a little too fluid |
| Viscosity of the composition before mixing, in cps | 7100 with M4 | 700 with M3 |
| Viscosity of the oxidizing composition in cps | 288 with M2 | |
| Viscosity of the composition after mixing with with the oxidizing composition for 2 min, in cps | 1700 with M3 | 135 with M2 |

Units of measurement in centipoises: cps

Both before and after mixing with the oxidant, Composition 3 according to the present disclosure was thicker and therefore posed less risk of running during application.

Dyeing Properties

Each mixture was applied to natural (NW) and permanent-waved (PW) locks of hair containing 90% white hairs, at a rate of 15 g of mixture per gram of locks of hair. After a leave-on time of 30 minutes at ambient temperature, the locks were rinsed, washed with a standard shampoo, rinsed again and dried.

The colorimetric measurements were carried out using the Konica Minolta CM-2600d spectrocolorimeter in the CIE L*a*b* system. In the L* a* b* system, L* represents the strength of the coloring obtained; the lower the value of L*, the stronger the coloring obtained. The chromaticity is measured by the values a* and b*, a* indicating the value along the green/red color axis and b* indicating the value along the blue/yellow color axis.

For each composition, the selectivity of the coloring was evaluated. The selectivity of the coloring is the variation in the color between natural hair and permanent-waved hair. The natural hair was representative of the nature of the hair at the root, whereas the permanent-waved hair was representative of the nature of the hair at the end.

The selectivity was measured by ΔE, which is the variation in color between the natural hair and the permanent-waved hair, and is obtained from the formula:

$$\Delta E = \sqrt{(L^* - L_o^*)^2 + (a^* - a_o^*)^2 + (b^* - b_o^*)^2}$$

in which:
L*, a* and b* represent the parameters of the dyed permanent-waved hair, and
$L_0^*$, $a_0^*$ and $b_0^*$ represent the parameters of the dyed natural hair.

The lower the value of ΔE, the lower the selectivity and therefore the more uniform the coloring along the hair.

Results

|  | Hair type | L* | a* | b* | ΔE |
|---|---|---|---|---|---|
| Composition 3 | NW dyed | 22.19 | 14.57 | −0.30 | 3.96 |
|  | PW dyed | 18.93 | 12.33 | −0.16 |  |
| Composition 4 | NW dyed | 26.25 | 16.83 | −0.31 | 5.99 |
|  | BP dyed | 20.95 | 14.04 | −0.45 |  |

On natural hair and permanent-waved hair, the coloring obtained with Composition 3 according to the present disclosure was stronger (lower L* values) than the coloring obtained with Composition 4.

The selectivity (ΔE) was lower for Composition 3 according to the present disclosure, which demonstrates a more uniform coloring along the fiber.

What is claimed is:

1. A dye composition for keratin fibers, comprising, in a medium suitable for dyeing:
   (A) at least one nonionic derivative of cellulose comprising at least one hydrophobic substituent containing from 8 to 30 carbon atoms;
   (B) at least one nonionic, nonhydrophobic polymer of the hydroxyalkylcellulose type chosen from hydroxypropylmethylcelluloses; and
   (C) at least one oxidation dye.

2. A dye composition according to claim 1, wherein the at least one nonionic derivative of cellulose (A) is chosen from hydroxyethylcelluloses substituted with the at least one hydrophobic substituent containing from 8 to 30 carbon atoms.

3. A dye composition according to claim 2, wherein the at least one hydrophobic substituent is chosen from $C_{10}$-$C_{22}$ alkyl groups.

4. A dye composition according to claim 3, wherein the at least one hydrophobic substituent is chosen from cetyl groups.

5. A dye composition according to claim 1, wherein the degree of hydrophobic substitution ranges from 0.1% to 10% by weight, of the total weight of the polymer.

6. A dye composition according to claim 5, wherein the degree of hydrophobic substitution ranges from 0.4% to 0.8% by weight, of the total weight of the polymer.

7. A dye composition according to claim 1, wherein the at least one nonionic derivative of cellulose (A) is present in an amount ranging from 0.01% to 10% by weight, relative to the total weight of the composition.

8. A dye composition according to claim 1, wherein the at least one nonionic derivative of cellulose (A) is present in an amount ranging from 0.1% to 1% by weight, relative to the total weight of the composition.

9. A dye composition according to claim 1, wherein the at least one nonionic, nonhydrophobic polymer of the hydroxyalkylcellulose type (B) is present in an amount ranging from 0.01% to 5% relative to the total weight of the composition.

10. A dye composition according to claim 9, wherein the at least one nonionic, nonhydrophobic polymer of the hydroxyalkylcellulose type (B) is present in an amount ranging from 0.1% to 1% by weight, relative to the total weight of the composition.

11. A dye composition according to claim 1 wherein the at least one oxidation dye (C) is chosen from oxidation bases, oxidation couplers, and addition salts thereof.

12. A dye composition according to claim 11, wherein the at least one oxidation base is chosen from para-phenylenediamines, bisphenylalkylenediamines, para-aminophenols, bis-para-aminophenols, ortho-aminophenols, heterocyclic bases, and addition salts thereof.

13. A dye composition according to claim 11, wherein the at least one oxidation base is present in a total amount ranging from 0.001% to 20% by weight relative to the total weight of the composition.

14. A dye composition according to claim 13, wherein the at least one oxidation base is present in a total amount ranging from 0.01% to 5% by weight relative to the total weight of the composition.

15. A dye composition according to claim 11, wherein the at least one oxidation coupler is chosen from benzene couplers, heterocyclic couplers, naphthalene couplers, and addition salts thereof.

16. A dye composition according to claim 15, wherein the at least one benzene coupler is chosen from meta-aminophenols, meta-phenylenediamines, meta-diphenols, and addition salts thereof.

17. A dye composition according to claim 11, wherein the at least one oxidation coupler is present in an amount ranging from 0.001% to 20% by weight relative to the total weight of the composition.

18. A dye composition according to claim 17, wherein the at least one oxidation coupler ranges from 0.01% to 5% by weight relative to the total weight of the composition.

19. A dye composition according to claim 1, further comprising at least one direct dye chosen from nitrobenzene dyes, azo direct dyes, methine direct dyes, anthraquinone dyes, xanthene dyes, triarylmethane dyes, and addition salts thereof.

20. A dye composition according to claim 1 further comprising at least one oxidizing agent.

21. A process for the oxidation dyeing of keratin fibers, comprising
applying to the keratin fibers, for a period of time sufficient to develop a desired color, a dye composition, in the presence of at least one oxidizing agent, wherein the dye composition comprises, in a medium suitable for dyeing:
(A) at least one nonionic derivative of cellulose comprising at least one hydrophobic substituent containing from 8 to 30 carbon atoms;
(B) at least one nonionic, nonhydrophobic polymer of the hydroxyalkylcellulose type chosen from hydroxypropylmethylcelluloses; and
(C) at least one oxidation dye.

22. A multicompartment device, comprising
at least one first compartment containing at least one dye composition, and
at least one second compartment containing at least one oxidizing agent, wherein the dye composition comprises, in a medium suitable for dyeing:
(A) at least one nonionic derivative of cellulose comprising at least one hydrophobic substituent containing from 8 to 30 carbon atoms;
(B) at least one nonionic, nonhydrophobic polymer of the hydroxyalkylcellulose type chosen from hydroxypropylmethylcelluloses; and
(C) at least one oxidation dye.

* * * * *